United States Patent [19]

Shibano et al.

[11] Patent Number: 6,013,288
[45] Date of Patent: Jan. 11, 2000

[54] PROCESS FOR MANUFACTURING BEER

[75] Inventors: Yuji Shibano; Hideko Yomo, both of Toyonaka; Takehiro Matsumoto, Ikeda; Hirofumi Koda, Osaka; Yoshihide Suwa, Ibaraki; Teruo Amachi, Takarazuka; Haruyo Hatanaka; Sakayu Shimizu, both of Kyoto, all of Japan

[73] Assignee: Suntory Limited, Osaka, Japan

[21] Appl. No.: 08/727,664

[22] PCT Filed: Feb. 16, 1996

[86] PCT No.: PCT/JP96/00346

§ 371 Date: Oct. 17, 1996

§ 102(e) Date: Oct. 17, 1996

[87] PCT Pub. No.: WO96/25483

PCT Pub. Date: Aug. 22, 1996

[30] Foreign Application Priority Data

Feb. 17, 1995 [JP] Japan ..................................... 7-29711

[51] Int. Cl.[7] .............................. C12C 11/00; C12C 7/00; C12C 7/28
[52] U.S. Cl. .................................. 426/16; 426/7; 426/11; 426/61; 426/59.2; 426/600; 435/93; 435/161
[58] Field of Search ..................................... 426/7, 11, 16, 426/61, 592, 600; 435/93, 161, 162

[56] References Cited

U.S. PATENT DOCUMENTS 3,947,605  3/1976  Chao .......................................... 426/656
4,601,986  7/1986  Wegner .................................... 435/255

FOREIGN PATENT DOCUMENTS 3-172180  7/1991  Japan .
4-27379  1/1992  Japan .
6-245750  9/1994  Japan .

OTHER PUBLICATIONS

Lee et al. 1986 J Amer Soc Brew Chem 44 (2) pp. 86–90, Feb. 1986.
Lee 1987 J Am Soc Brew Chem 45 (4) pp.131–135, Apr. 1986.
Prentice 1988 J Am Soc Brew Chem 46 (3) pp. 92–96, Mar. 1, 1988.

*Primary Examiner*—Lynette F. Smith
*Assistant Examiner*—Mary K Zeman
*Attorney, Agent, or Firm*—Burns, Doane, Swecker & Mathis, L.L.P.

[57] ABSTRACT

A process for manufacturing beer having a reduced content of purine compounds by using wort having a reduced content of purine nucleosides as a result of decomposing purine nucleosides into purine bases by using nucleoside phosphorylase or nucleosidase, or decomposing purine nucleosides into purine bases during fermentation and having the purine bases metabolized by yeast.

19 Claims, 8 Drawing Sheets

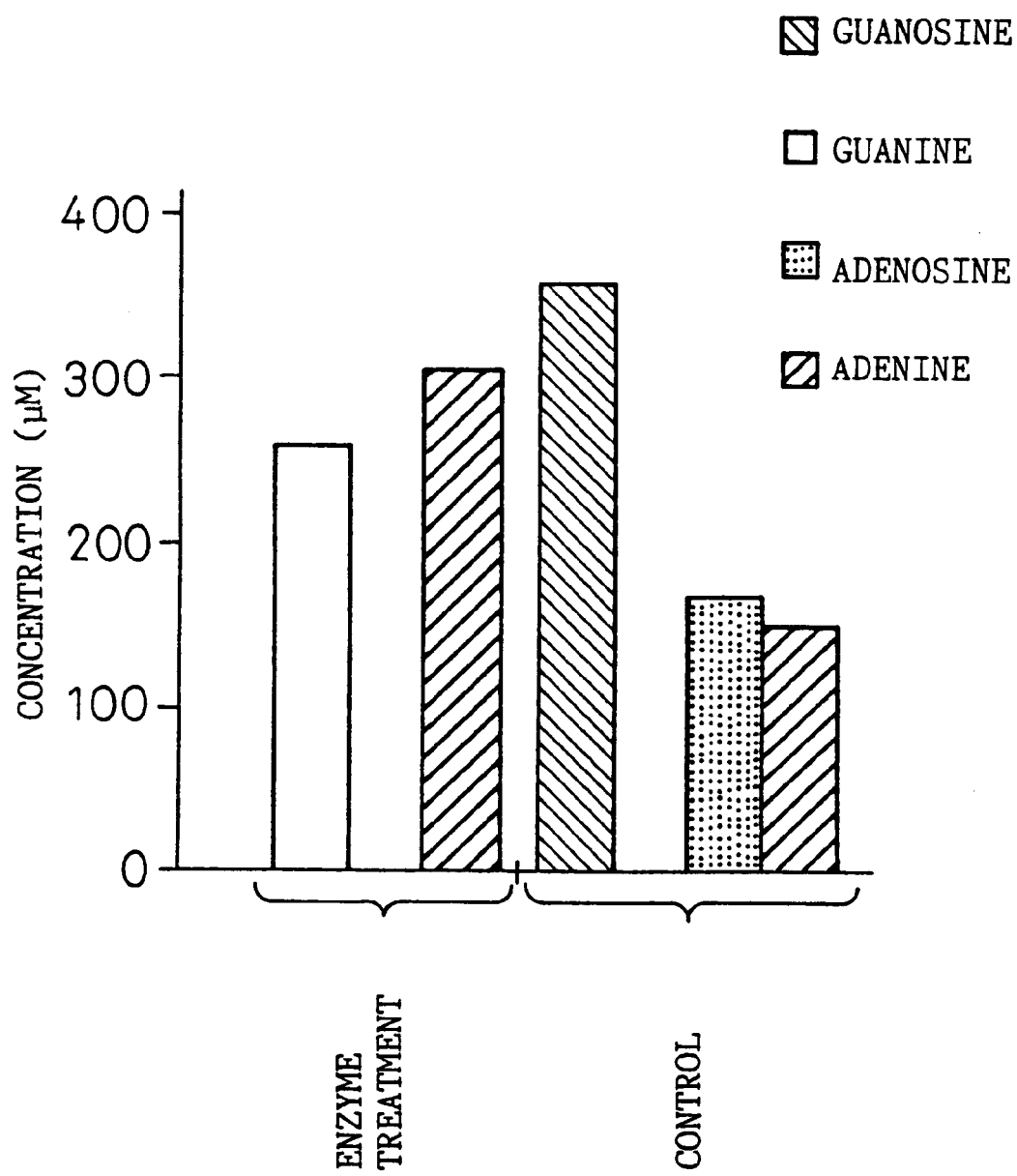

PROCESS FOR MANUFACTURING BEER

FIELD OF THE INVENTION

The present invention relates to a process for manufacturing beer in which the concentration of purine compounds is reduced. More specifically, the present invention relates to a process for manufacturing beer characterized by acting enzyme on purine nucleosides contained in the wort to decompose them into purine bases that can be assimilated by yeast.

BACKGROUND ART

In recent years, increases have been observed in blood uric acid levels accompanying the Westernization of the diet and overnutrition. There is therefore concern over increases in the occurrence of gout caused by asymptomatic hyperuricemia. Purine bases, purine nucleosides, purine nucleotides and high molecular weight nucleic acids in the diet are digested and absorbed in the digestive tract, and are decomposed into uric acid by the purine decomposing system in the liver. There are numerous epidemiological findings that indicate that ingestion of a diet having a high content of purine compounds is the cause of hyperuricemia and gout. Decreasing an amount of purine compounds ingested is therefore considered to be the most important means for preventing hyperuricemia or gout.

Examples of foods containing large amounts of purine compounds include meat, soft roe, fish eggs and liver. However alcoholic beverages, and particularly beer, also have a considerably high content of purine compounds. In actuality, Kaneko (Kiyoko Kaneko; Nippon Rinsho, 49: 1108–1115 (1991)) conducted a comparison of the purine compound contents of various alcoholic beverages. It was reported that fermented alcoholic beverages such as beer, sake and wine have a higher purine compound content than distilled alcoholic beverages such as whiskey and Shochu, and that beer has the highest purine compound content among fermented alcoholic beverages. Fujimori, et al. reported that a total of 50 to 70 mg/liter of purine compounds are contained in beer (Fujimori, et al., Nyosan, Vol. 9, No. 2, pp. 128–133).

Furthermore, this value was determined by hydrolyzing the purine compounds contained in beer into purine bases with perchloric acid, and then measuring the resulting purine bases with high-performance liquid chromatography.

Although the purine compound content in beer is within the range of $\frac{1}{100}$ to $\frac{1}{10}$ that of the above-mentioned meat, eggs and liver, since beer is consumed in large amounts, it should be considered to present a greater risk of morbidity for hyperuricemia and gout than distilled alcoholic beverages. Tofler and Woodings (O. B. Tofler and T. L. Woodings; Med. J. Aust. 2, 479–481 (1981)) conducted a 13-year study by grouping subjects into study groups according to the amount of beer consumption, and pointed out the existence of a correlation between the amount of beer consumed and the incidence of gout. Thus, according to the findings of epidemiological studies, beer is currently regarded as presenting the highest risk of morbidity for hyperuricemia and gout among alcoholic beverages.

DISCLOSURE OF THE INVENTION

Thus, the present invention provides a process for manufacturing beer having a reduced content of purine compounds.

The inventors of the present invention obtaining findings that beer can be manufactured to have a reduced content of purine compounds by decomposing purine nucleosides contained in wort into purine bases, and as a result of further research, were able to complete the present invention.

Namely, the present invention provides a process for manufacturing beer characterized in that nucleoside-decomposed wort is produced by causing nucleoside phosphorylase or nucleosidase to act on wort to decompose the purine nucleosides contained in the wort into purine bases, and beer is manufactured using said nucleoside-decomposed wort.

Moreover, the present invention provides a process for manufacturing wort characterized by causing nucleoside phosphorylase or nucleosidase to act on wort.

BRIEF DESCRIPTION OF THE DRAWINGS

FIG. 10 shows the results of analyzing purines in wort produced by adding enzyme and wort produced without adding enzyme.

DETAILED DESCRIPTION

Figure 1:
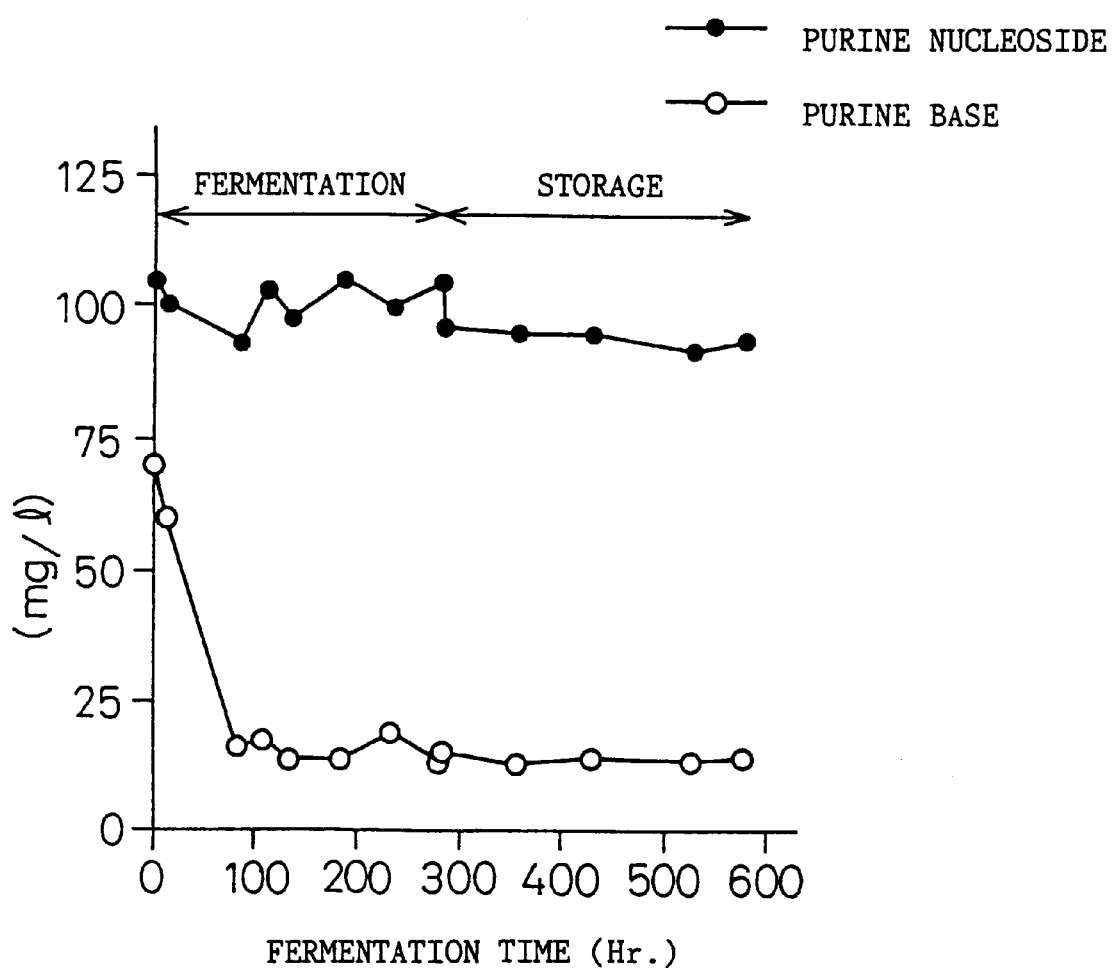
FIG. 1 is a graph showing the consumption of purine compounds in trial beer brewing on a 70 liter scale. Black dots indicate purine nucleosides, while white dots indicate purine bases.

The present inventors completed the present invention as a result of conducting research, for the purpose of providing a process for manufacturing beer in which the concentration of purine compounds is reduced, by measuring the amounts of purine nucleosides, purine nucleotides, purine bases and high molecular weight nucleic acids in beer. Purine base is the generic term for derivatives of purine(9H-imidazo[4,5-d]pyrimidine) having various substituted portions, examples of which include adenine, guanine and xanthine.

Purine nucleoside is the generic term for glycosides wherein a purine base and the reducing group of a sugar molecule is linked by an N-glycoside bond, examples of which include adenosine, guanosine and inosine.

Purine nucleotide is the generic term for compounds in which the sugar portion of a purine nucleoside and phosphoric acid form an ester bond, examples of which include adenylic acid, guanylic acid and inosinic acid.

Purine compound is the generic term for compounds containing a purine skeleton, such as the above-mentioned purine bases, purine nucleosides and purine nucleotides.

The present inventors clarified the following points as a result of measuring the amount of each purine compound in beer and its production process.

1) Although the amount of purine compounds in various brands of commercially available beers fluctuates within the range of 40 to 100 mg/liter, the amount of purine nucleosides is 2 to 25 times the amount of purine bases. Namely, the majority of purine compounds contained in beer are purine nucleosides.

2) In the fermentation process, purine bases contained in the wort are taken up and metabolized by the yeast until they are essentially absent.

As a result of conducting earnest research for solve this problem on the basis of the above-mentioned analytical results, the present inventors invented a process for manufacturing beer having a reduce amount of purine compounds.

In other words, although normal yeast is unable to take up purine nucleosides, they are able to take up and metabolize purine bases. In the present invention, therefore, by causing an enzyme to act on wort, decomposing the purine nucleosides contained in the wort to purine bases to produce a nucleoside-decomposed wort, and using this nucleoside-decomposed wort, the amount of purine compounds contained in beer can be reduced. Furthermore, in the nucleoside-decomposed wort, a portion or all of the purine nucleosides in the wort are decomposed to purine bases by the enzyme. Although the purine nucleoside content in this nucleoside-decomposed wort can be adjusted according to the amount of enzyme added, reaction time, reaction temperature and so forth, preferably all of the purine nucleosides are decomposed to purine salts to produce a wort that is free of purine nucleosides.

This enzyme can act (1) in the wort production process, (2) after the wort production process and before the fermentation process, or (3) in the fermentation process. Enzyme can be added at the start of wort production (saccharification) or a suitable time during wort production. In order for the enzyme to act before the fermentation process, enzyme should be added to the wort during the wort production process a prescribed amount of time before the start of fermentation. It is most preferable, however, that enzyme be added before boiling during the wort production process. This is because, since the enzyme can be inactivated by boiling, active enzyme cannot be introduced into the finished beer and there is no possibility of the enzyme having any effect on quality.

In addition, in order for the enzyme to act in the fermentation process, enzyme is added either before the start of fermentation or during fermentation. However, since it is necessary that purine bases formed by the action of the enzyme be metabolized and broken down by yeast, it is preferable that the enzyme be added at the start of fermentation or in the first half of the fermentation period.

Wort is acidic (pH 5.0–5.5) through its production process, and since the temperature of the production process is 50–80° C., an enzyme is preferable that is able to react in an acidic range and at high temperatures.

Enzymes for this purpose may be derived from malt or other sources, for example nucleoside phosphorylase or nucleosidase. Examples of enzymes from sources other than malt that can be used include nucleoside phosphorylase (EC 2.4.2.1) derived from calf spleen and bacteria.

The nucleosidase used in the present invention refers to that which decomposes purine nucleosides into purine bases and ribose, and preferably has an optimum pH range of 4.5 to 6.5 and an optimum temperature range of 50° C. to 80° C. There are no particular limitations on the type of inhibitor, Km value or molecular weight and so forth that express other general properties of the enzyme.

Nucleosidase is normally produced by culturing a microorganism strain that has the ability to produce nucleosidase. Examples of such strains of microorganisms that are used include the genera Ochrobactrum, Streptococcus, Pediococcus, Leuconostoc, Lactobacillus, Escherichia, Citrobacter, Serratia, Alcaligenes, Flavobacterium, Bacillus, Corynebacterium, Staphylococcus, Arthrobacter, Comamonas, Pseudomonas, Kluyveromyces, Saccharomyces, Debaryomyces, Pichia, Hansenula, Sporobolomyces, Sporidiobolus, Aspergillus and Pencillium. There are no particular limitations on the strain, and even strains freshly isolated from soil, lactic acid bacteria, rancid foods or animal organs or excrement have no problem with their use provided they have the ability to produce nucleosidase. In addition, even these strains mutated artificially by subjecting to ultraviolet radiation or treatment with mutation agents, or wherein the gene fragment required for expression of said nucleosidase activity is artificially removed and incorporated in another transformant, can still be used in the process of the present invention.

Specific examples of strains of microorganisms that are able to produce nucleosidase include *Ochrobactrum anthropi* (FERM BP-5377), *Streptococcus citrovorum, Pediococcus pentosaceus* (IFO 3182), *Leuconostoc dextranicum, Lactobacillus plantarum, Lactobacillus arabinosus* (IFO 3070), *Lactobacillus plantarum, Lactobacillus cucumeris* (IFO 3074), *Escherichia coli* B biotin-less, *Citrobacter freundii* (IFO 13546), *Serratia marcescens* (IFO 3736), *Alcaligenes faecalis, Flavobacterium meningosepticum* (DSM 2800), *Bacillus cereus, Corynebacterium glutamicum, Staphylococcus aureus* (IFO 3060), *Arthrobacter ureafaciens, Arthrobacter globiformis* (IFO 12140), *Comamonas testosteroni, Pseudomonas dacunhae* (IFO 12048), *Pseudomonas putida, Bacillus aneurinolyticus, Bacillus thuringiensis* (IFO 3951), *Kluyveromyces marxianus, Saccharomyces maxianus* (IFO 0277), *Debaryomyces pseudopolymorphus, Pichia pseudopolymorpha* (IFO 1026), *Pichia capsulata, Hansenula capsulata* (IFO 0721), *Sporobolomyces salmonicolor* (IFO 1038), *Sporidiobolus salmonicolor, Sporobolomyces odorus* (IFO 1035), *Aspergillus niger* (IFO 4416), *Penicillium spinulosum* (IFO 4033), *Aspergillus oryzae* (IAM 2630), *Aspergillus flavus* (IFO 5839), *Aspergillus terreus* (IFO 5445), *Aspergillus sojae* (IFO 4386), *Aspergillus parasiticus* (IFO 4082) and Penicillium species. However, particularly preferable examples are *Ochrobactrum anthropi* (FERM BP-5377), *Aspergillus niger* (IFO 4416), *Aspergillus oryzae* (IAM 2630), *Aspergillus flavus* (IFO 5839) and *Aspergillus terreus* (IFO 5445).

Furthermore, those of the above-mentioned strains that are shown with an ATCC number can be acquired from ATCC, while those shown with an IFO number can be acquired from the Fermentation Research Institute (2-17-85, Jusohonmachi-cho, Yodogawa-ku, Osaka).

Furthermore, a bacterial strain newly isolated in the present invention *Ochrobactrum anthropi* has the following toxonomical properties.

(a) Morphological Properties
  (1) Cell form: Rods
  (2) Cell polymorphism: No
  (3) Motility: Yes
  (4) Spores: No
(b) Culturing Properties
  (1) Culturing on beef broth agar plates (30° C., 2 days): Colonies appear circular with protrusions. The colony surface is smooth and glossy.
(c) Physiological Properties
  (1) Gram staining: Negative
  (2) Nitrate reduction: Negative
  (3) Denitrification reaction: Negative
  (4) Indole formation: Negative
  (5) Acid formation from glucose: Negative
  (6) Urease: Positive
  (7) Cytochrome oxidase: Positive
  (8) Catalase: Positive
  (9) Acid formation from xylose: Positive
  (10) Optimum growth temperature: 28–37° C.
  (11) Pigment formation on King's B medium: Negative
  (12) O-F test (sugar: glucose): Oxidation
  (13) Sugar assimilation:
    (1) Glucose: +
    (2) Arab(2) Arabinose: +
    (3) Mannose: +
    (4) Mannitol: −
    (5) N-acetylglucosamine: +
    (6) Maltose: +
    (7) Gluconate: −
    (8) Caprate: +
    (9) Adipate: −
    (10) Malate: +
    (11) Citrate: +
    (12) Phenylacetate: −
(d) Other Properties
  (1) Esculin hydrolysis: Negative
  (2) β-galactosidase: Negative
  (3) Gelatin hydrolysis: Negative
  (4) Arginine dihydrolase: Positive
  (5) Growth on MacConkey's medium: Positive
  (6) Polymyxin sensitivity: Negative
  (7) Analine utilization: Positive
  (8) Glycine utilization: Positive Physiological and biochemical properties were investigated using Apizone (Bio Merieux S.A.). Moreover, when species name was determined using the Apizone Analytical Profile Index based on those results, although nitrate reduction and glycine utilization were different from the description of Holmes et al. (International Journal of Systematic Bacteriology, Vol. 38, No. 4, 1988, p. 406–416), the bacterium was identified as *Ochrobactrum anthropi* according to the Index.

This strain was identified as *Ochrobactrum anthropi*. This bacterial strain was deposited as an international deposition under the Budapest Treaty on Jan. 26, 1996 at the Institute of Bioscience and Human-Technology Agency of Industrial Science and Technology as FERM BP-5377.

Routine stationary culture, shaking culture, aerating and stirring culture or solid culturing, either continuously or intermittently, can be performed to culture these microorganism strains and to produce nucleosidase. In addition, nucleosidase is normally contained in the microorganism after culturing, and a crude or purified enzyme, having improved specific activity over the natural form, can be obtained by routine enzyme purification means and used in the process of the present invention. In addition, in the case nucleosidase is secreted into the culture liquid, said culture liquid may also be used as is.

EXAMPLES

Although the following provides a detailed explanation of the present invention through its Examples, the present invention is not limited to these Examples.

Experiment 1

Measurement of Purine Compounds in Beer

Purine compounds in beer were analyzed using the Model EP-10 high-performance liquid chromatograph (Eicom). The GS320-H (7.6 mm D×250 mm L, Asahipack) was used for the column, 10 mM sodium phosphate (pH 5.0) was used for the mobile layer, the flow rate was 1.0 ml/min, and analysis was performed at 30° C. After removing any solids by passing through a membrane filter, 10 μl of sample were injected, and the amount of purine compounds was determined by the absorbance at 260 nm.

Known concentrations of 3 types of purine bases (adenine, guanine and xanthine) and 3 types of purine nucleosides (adenosine, guanosine and inosine) were analyzed in advance as reference samples followed by determination of retention time and peak surface area for each purine compound. Identification of each purine compound in actual samples was determined based on the retention time of each peak, while concentration was determined from a calibration curve determined from the peak surface areas of known concentrations of reference samples. Furthermore, since 3 types of purine nucleotides (adenylic acid, guanylic acid and inosinic acid) elute much faster under these analytical conditions, they do not interfere with analysis of the above-mentioned 6 types of purine compounds.

The analytical results for 7 types of beers and 2 types of wines, all commercially available, are shown in Table 1. The total amount of purines, as indicated by the sum of purine bases and purine nucleosides, converted into an amount of purine bases, was 40 to 100 mg/liter although varying according to the type of beer. In addition, the majority of purine compounds were in the form of nucleosides.

Wine, which is also a fermented alcoholic beverage in the same manner as beer, exhibited a high purine content of 60 mg/liter for red wine, and a lower value of 20 mg/liter for white wine.

TABLE 1

| Product | Adenosine | Guanosine | Inosine | Adenine | Guanine | Xanthine | Purine bases (mg/liter) | Purines in nucleosides | Total purines |
|---|---|---|---|---|---|---|---|---|---|
| Beer A | 18.4 | 37.1 | 19.5 | 4.2 | 1.9 | 8.0 | 14.1 | 39.0 | 53.1 |
| Beer B | 15.5 | 32.1 | 15.2 | 4.9 | 7.8 | 4.7 | 17.4 | 32.6 | 50.0 |
| Beer C | 7.8 | 34.2 | 19.1 | 5.5 | 3.1 | 8.8 | 17.4 | 31.8 | 49.2 |
| Beer D | 8.1 | 36.9 | 20.5 | 6.6 | 3.9 | 7.8 | 18.3 | 34.2 | 52.5 |
| Beer E | 5.0 | 35.4 | 19.4 | 6.7 | 3.8 | 8.6 | 19.1 | 31.2 | 50.3 |
| Beer F | 6.6 | 32.2 | 17.2 | 6.6 | 5.3 | n.d. | 11.9 | 29.2 | 41.1 |
| Beer G | 16.2 | 136.4 | 40.8 | 4.0 | n.d. | n.d. | 4.0 | 101.7 | 105.7 |
| Red wine H | 0.5 | 1.3 | 12.6 | 34.3 | 20.0 | n.d. | 54.3 | 7.4 | 61.7 |
| White wine I | 0.3 | 7.0 | 9.8 | n.d | n.d | 14.0 | 14.0 | 8.9 | 22.9 |

Furthermore, when the purine nucleotides in beer and wort were analyzed with an ion exchange column, purine nucleotides were not present in the beer or wort. In addition, even when the beer and wort were analyzed by acid hydrolysis, since there was no change in the total amount of purine compounds before and after acid hydrolysis, high molecular weight nucleic acids such as RNA and DNA are considered to not be present in beer and wort.

Experiment 2

Consumption of Purine Compounds in the Beer Production Process

The consumption of purine compounds in a beer production process was investigated in trial brewing on a 70 liter scale. The concentration of the initial extract was 12.5%, the amount of yeast added was 5 g wet weight/liter, and the fermentation temperature was 11.5° C. Yeast that settled to the bottom of the fermentor at the point the extract reached 2.5% (260 hours after the start of fermentation) was removed, the temperature was lowered to 0° C. and storage was performed for another 300 hours.

Those results are shown in FIG. 1. The total of adenosine, guanosine and inosine was indicated as the amount of purine nucleosides, and the total of adenine, guanine and xanthine was indicated as the amount of purine bases. Although purine bases were present in the wort at approximately 70 mg/liter, that amount decreased to 10 mg/liter in the initial stage of fermentation, and did not increase after that time during fermentation and storage. On the other hand, a large amount of purine nucleosides were present in the wort at approximately 90 mg/liter, and this amount did not change during fermentation or storage.

These results indicate that purine bases contained in normal wort are uptaken and metabolized by yeast and essentially disappear in the yeast growth phase in the initial stage of fermentation.

Example 1

Decomposition of Purine Bases by Nucleoside Phosphorylase

Nucleoside phosphorylase derived from calf spleen (Boehringer) was added to wort having an extract concentration of 12.5% to a concentration of 7 units/ml, and allowed to react for 3 hours at 30° C. The amount of purine compounds in the wort to which enzyme was added and a wort held for 3 hours at 30° C. without adding enzyme as the control were measured using the method described in Experiment 1.

Figure 2:
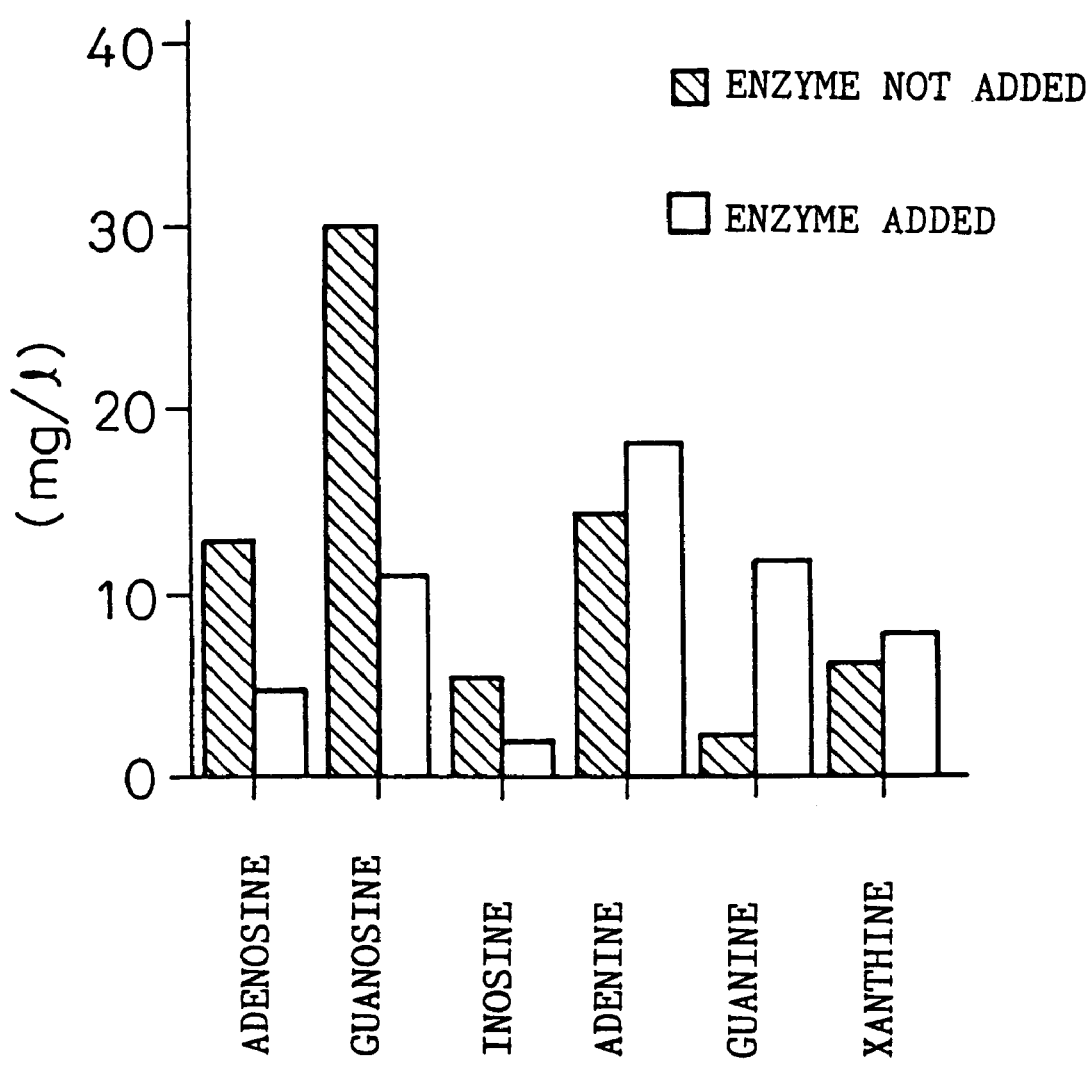
FIG. 2 is a bar graph showing the amount of each purine compound when nucleoside phosphorylase was added to wort.

As shown in FIG. 2, the amounts of all purine nucleosides of adenosine, guanosine and inosine decreased in the wort containing enzyme in comparison with the wort to which enzyme was not added, and the amounts of the purine bases of adenine, guanine and xanthine increased correspondingly. Furthermore, the decomposition ratio of each purine nucleoside was roughly 60%.

These results indicate that nucleoside phosphorylase derived from calf spleen is effective in decomposing purine nucleosides in wort. According to the results of Experiment 2, since purine bases are uptaken and metabolized by yeast during the yeast growth phase of initial fermentation, purine bases obtained by decomposing purine nucleosides with nucleoside phosphorylase were also uptaken and metabolized by yeast during fermentation. Thus, these results show that if beer is manufactured using wort treated with this enzyme, the purine nucleoside content of the beer can be reduced by roughly 60%.

Moreover, since the beer indicated in Experiment 2 contains 90 mg/liter of purine nucleosides and 10 mg/liter of purine bases, the purine nucleoside content of the beer can be reduced to half by treating the wort with this enzyme.

Example 2

Screening of Nucleosidase Able to be Used in the Wort Production Process

Nucleosidase was screened from molds, bacteria and yeast using the procedure described below.

Each strain was cultured and collected using the media and culturing conditions listed below. After suspending the cells in pH 7.4 20 mM Tris-HCl buffer, the cells were homogenized by ultrasonic homogenization (molds were crushed in a mortar with sea sand) and contaminants were removed by centrifugation to obtain the crude enzyme liquid. The crude enzyme was reacted at 60° C. and 70° C. in pH 4.5 100 mM sodium acetate buffer in the presence of substrate consisting of 5 mM inosine, adenosine or guanosine. The resulting solution was spotted on a silica gel thin layer plate after which thin layer chromatography was performed using a developing solution consisting of normal butanol, acetic acid and water in the ratio of 3:1:1. The degree of decomposition of the nucleoside was investigated based on the size of the nucleoside spot and the corresponding purine base spot. The results for microorganisms exhibiting high activity are shown in Table 2.

Media Composition and Culturing Conditions

1)

Molds
Malt extract 5% 28° C., 3–5 days
Yeast extract 0.3% Shake culturing
pH 5.5

2)

Bacteria (excluding lactic acid bacteria)
Tryptone 0.5% 28° C. , 2–4 days
Yeast extract 0.5% Shake culturing
Glucose 0.1%
Dipotassium phosphate 0.1%
pH 7.0

3)

Lactic Acid Bacteria
Peptone 1% 28° C., 4–7 days
Beef extract 1% Still culturing
Yeast extract 0.5%
Glucose 2%
Span 80 0.1%
Ammonium citrate 0.2%
Sodium acetate 0.5%
Magnesium sulfate-7 hydrate 0.01%
Manganese chloride-4 hydrate 0.005%
Dipotassium phosphate 0.2%
pH 6.5

4)

Yeast
Yeast extract 0.2% 28° C., 2–4 days
Peptone 0.5% Shake culturing
Glucose 5%
Dipotassium phosphate 0.4%
Monopotassium phosphate 0.2%
Magnesium sulfate-7 hydrate 0.02%
pH 6.0

TABLE 2

| Strain | Activity | | | | | |
| --- | --- | --- | --- | --- | --- | --- |
| | Adenosine | Inosine | Guanosine | Adenosine | Inosine | Guanosine |
| Streptococcus citrovorum | ⊚ | ○ | X | Δ | Δ | X |
| Pediococcus pentosaceus | ⊚ | ⊚ | ⊚ | ○ | Δ | X |
| Leuconostoc dextranicum | | ⊚ | ⊚ | ⊚ | Δ | ΔΔ |
| Lactobacillus plantarum (Lactobacillus arabinosus) | Δ | X | ⊚ | Δ | Δ | Δ |
| Lactobacillus plantarum (Lactobacillus cucumeris) | ⊚ | X | X | Δ | X | X |
| Escherichia coli B biotin less | ⊚ | ⊚ | X | ⊚ | ⊚ | ○ |
| Citrobacter freundii | ⊚ | ⊚ | X | ⊚ | ⊚ | X |
| Serratia marcescens | ⊚ | ⊚ | X | ⊚ | ⊚ | Δ |
| Alcaligenes faecalis | ⊚ | ⊚ | X | ⊚ | ⊚ | ○ |
| Flavobacterium meningosepticum | ⊚ | ⊚ | Δ | ⊚ | ⊚ | ○ |
| Bacillus cereus | ⊚ | ⊚ | X | ⊚ | ⊚ | Δ |
| Corynebacterium glutamicum | ⊚ | ⊚ | X | ⊚ | ⊚ | X |
| Staphylococcus aureus | ⊚ | ⊚ | X | ⊚ | ⊚ | X |
| Arthrobacter ureafaciens (Arthrobacter globiformis) | ⊚ | ⊚ | X | ⊚ | ⊚ | X |
| Comamonas testosteroni (Pseudomonas dacunhae) | ⊚ | ⊚ | X | ⊚ | ⊚ | ○ |
| Ochrobactrum anthropi | ⊚ | ⊚ | ⊚ | X | ⊚ | ⊚ |
| Pseudomonas putida | ⊚ | ⊚ | X | ⊚ | ⊚ | X |
| Bacillus aneurinolyticus | Δ | X | X | X | Δ | X |
| Bacillus thuringiensis | ⊚ | Δ | X | Δ | Δ | X |
| Kluyveromyces marxianus (Saccharomoyces maxianus) | Δ | ○ | X | X | Δ | X |
| Debaryomyces pseudopolymorphus (Pichia pseudopolymorpha) | Δ | ○ | X | X | Δ | X |
| Pichia cupsuluta (Hansenula capsulata) | Δ | ○ | X | X | Δ | X |
| Sporobolomyces salmonicolor | Δ | ○ | Δ | Δ | Δ | X |
| Sporidiobolus salmonicolor (Sporobolomyces odorus) | Δ | ○ | Δ | Δ | Δ | X |
| Aspergillus niger | ○ | ⊚ | Δ | ○ | Δ | X |
| Penicillium spinulosum | Δ | ○ | Δ | ○ | ○ | X |
| Aspergillus awamori | Δ | ○ | Δ | Δ | X | X |
| Aspergillus oryzae | ○ | ⊚ | ○ | Δ | ○ | X |
| Aspergillus flavus | ○ | ⊚ | Δ | ○ | ○ | X |
| Aspergillus terreus | ○ | ⊚ | Δ | ○ | ○ | Δ |
| Aspergillus sojae | ○ | ⊚ | ○ | X | Δ | X |
| Aspergillus parasiticus | ○ | ⊚ | ○ | Δ | Δ | X |
| Penicillium sp. | ○ | ○ | Δ | ○ | ○ | Δ |

⊚ > 70%, ○ > 50%, Δ > 20%, X < 10%

11

Example 3

Properties of Nucleosidase

Among the microorganisms acquired above, the bacterium *Ochrobactrum anthropi* produced nucleosidase having high activity and able to decompose inosine, adenosine and guanosine at 60° C. and inosine and guanosine at 70° C. The crude enzyme liquid of *Ochrobactrum anthropi* was dialyzed against pH 6.0 50 mM MES buffer, and after removing the low molecular weight substances in the crude enzyme liquid, the properties of the nucleosidase were investigated in detail.

Activity Assay Method Using Inosine

195 µl of 25 mM suitable buffer (sodium acetate buffer pH 4.5–5.0, Tris-HCl buffer pH 7.0–9.5, MES buffer pH 5.5–6.5) and 5 mM inosine solution were incubated in advance at each temperature. 5 µl of enzyme solution were added to start the reaction. Ten minutes later, 200 µl of 0.2 N hydrochloric acid solution were added to stop the reaction, and the denatured protein was removed by centrifugation. 100 µl of the supernatant, 100 µl of 0.1 N sodium hydroxide solution, 50 µl of pH 8.0 1 M Tris-HCl buffer and 345 µl of water were mixed and the absorbance was measured at 293 nm. This was used as the control. Moreover, 5 µl (5 mU) of xanthine oxidase were added and mixed, and absorbance was measured when the increase in absorbance at 293 nm stopped. The unit U used for nucleosidase activity represents the amount of enzyme that hydrolyzes 1 µmol of nucleoside in 1 minute. The activity (U/ml) of the nucleosidase of the enzyme liquid was determined 3.33×ΔA293. Furthermore, ΔA293 refers to the value resulting from subtracting the absorbance of the control from the absorbance of that to which xanthine oxidase has been added.

Activity Assay Method by Reducing Sugar Quantification

195 µl of pH 5.0 25 mM sodium acetate buffer and 5 mM nucleoside solution were incubated in advance at each temperature. 5 µl of enzyme solution were added to start the reaction. Ten minutes later, 200 µl of 0.1 N zinc sulfate solution were added to stop the reaction. Moreover, 200 µl of 0.1 N sodium hydroxide solution were added followed by centrifugation to remove protein. 200 µl of the supernatant, 300 µl of a 4% sodium carbonate, 1.6% glycine and 0.045% copper sulfate-5 hydrate solution, 0.9 ml of 0.04% 2,9-dimethyl-1,10-phenanthroline and 200 µl of water were mixed followed by incubation for 8 minutes at 95° C. Absorbance was measured at 450 nm. A calibration curve was prepared from the absorbance at 450 nm after performing similar treatment using a ribose solution of known concentration, and ribose concentration of the enzyme reaction liquid was calculated. The activity of the nucleosidase of the enzyme liquid (U/ml) was determined at the ribose concentration (µM)×0.004.

(1) Optimum Temperature

Figure 3:
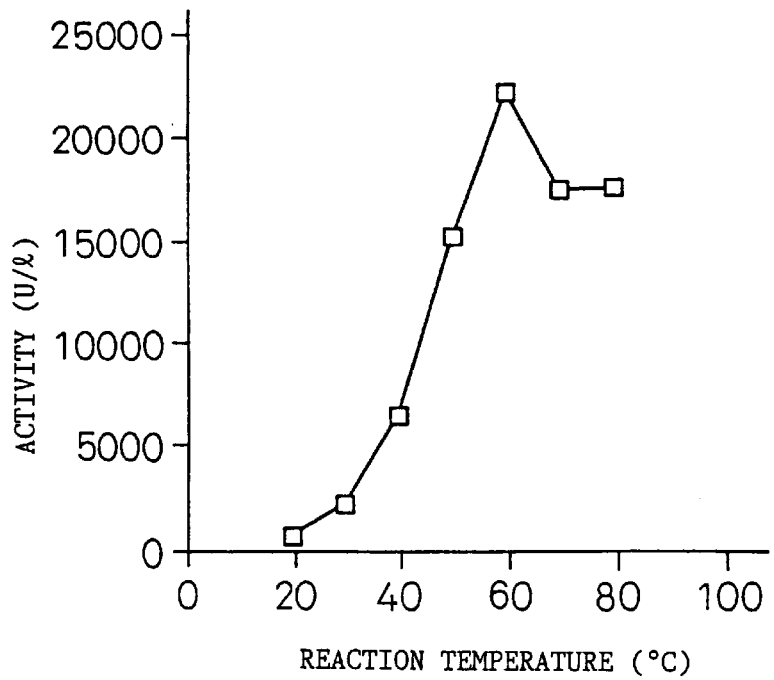
FIG. 3 shows the activity when inosine is used as substrate at pH 5.0 and the reaction is carried out for 10 minutes at each temperature.

Optimum temperature: 50–80° C. Activity when enzyme was allowed to react for 10 minutes at each temperature and pH 5.0 using inosine for the substrate is shown in FIG. 3. Although activity was the highest at 60° C. and decreased to about 80% maximum at 70° C., the activity remained unchanged even at 80° C.

(2) Optimum pH

Figure 4:
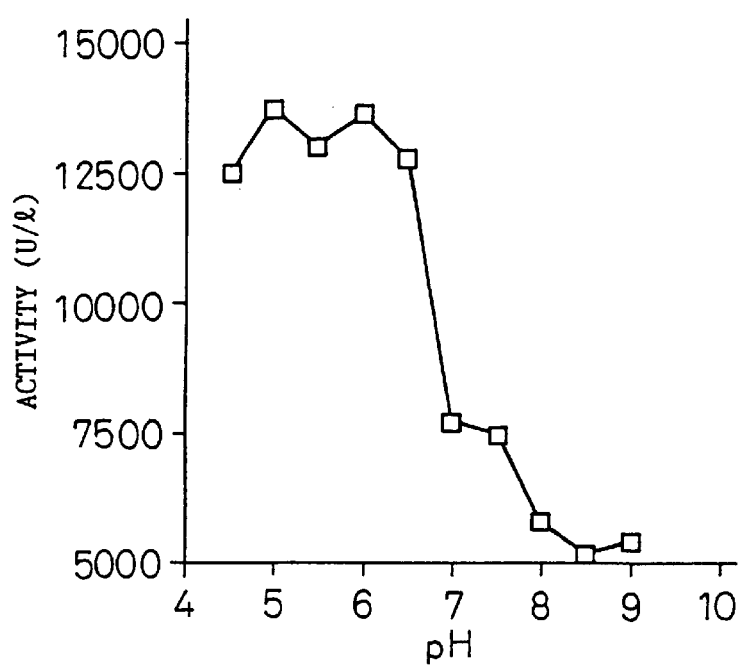
FIG. 4 shows the activity when inosine is used as substrate, an equal amount of 10 mM inosine solution is added after incubating for each time at 70° C. and at each pH, and the reaction is carried for 10 minutes at 70° C.

Optimum pH: 4.5–6.5. Activity when enzyme was allowed to react for 10 minutes and 70° C. at each pH using inosine for the substrate is shown in FIG. 4. Peak activity was observed at pH 5.0 and 6.0.

(3) Heat Resistance

Figure 5:
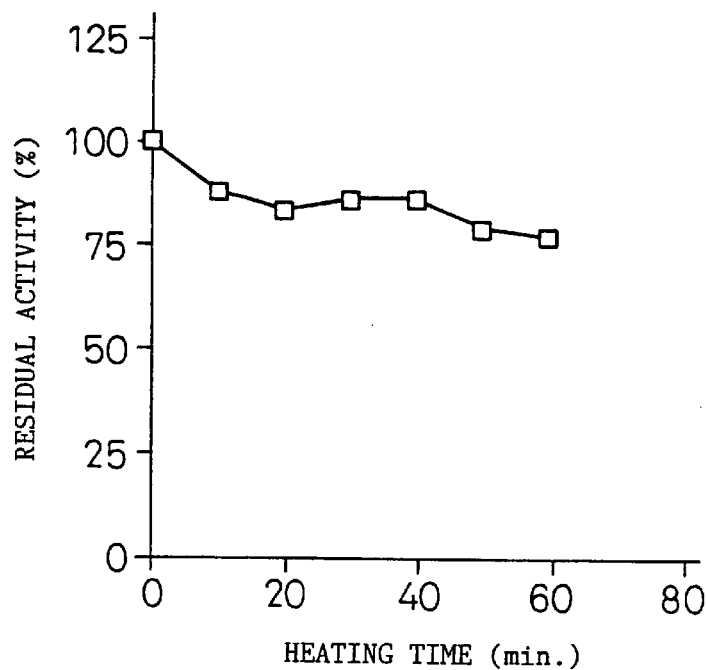
FIG. 5 shows the activity when an equal amount of 10 mM inosine solution is added after incubating for each time at 70° C. in pH 5.0 50 mM sodium acetate buffer, and the reaction is carried out for 10 minutes at 70° C.
Figure 6:
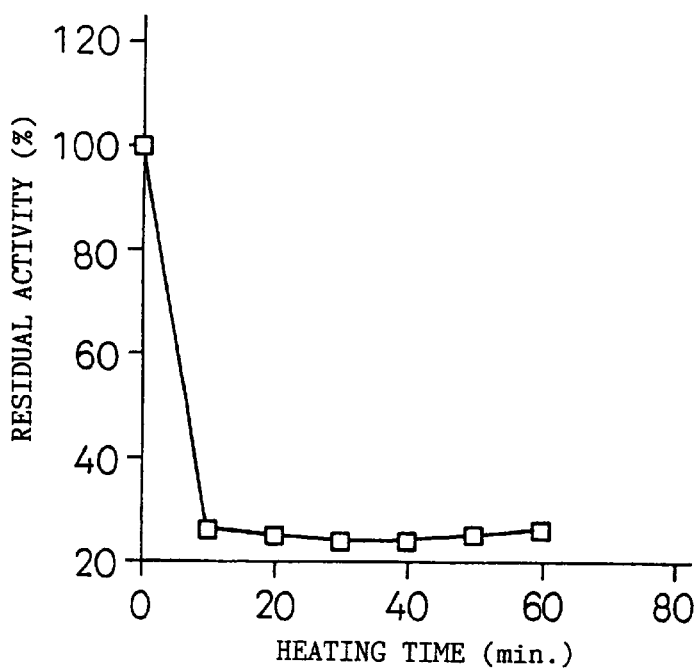
FIG. 6 shows the activity when an equal amount of 10 mM inosine solution is added after incubating for each time at 70° C. in pH 5.0 50 mM sodium acetate buffer, and the reaction is carried out for 10 minutes at 40° C.

After incubating for each time at 70° C. in pH 5.0, 50 mM sodium acetate buffer, an equal volume of 10 mM inosine solution was added and allowed to react for 10 minutes at 70° C. That activity is shown in FIG. 5. In addition, the activity when allowed to react for 10 minutes at 40° C. is shown in FIG. 6. In the case of reacting at 70° C. in heat treatment for 10 minutes, although activity decreased to about 70%, it hardly decreased at all after that time. In the case of reacting at 40° C., in a heat treatment, for 10 minutes, although activity decreased to about 25%, it hardly decreased at all after that time.

In consideration of the results of (1) through (3), *Ochrobactrum anthropi* is expected to have at least two types of nucleosidases having different optimum temperatures, optimum pH and heat resistance.

(4) Substrate Specificity

Figure 7:
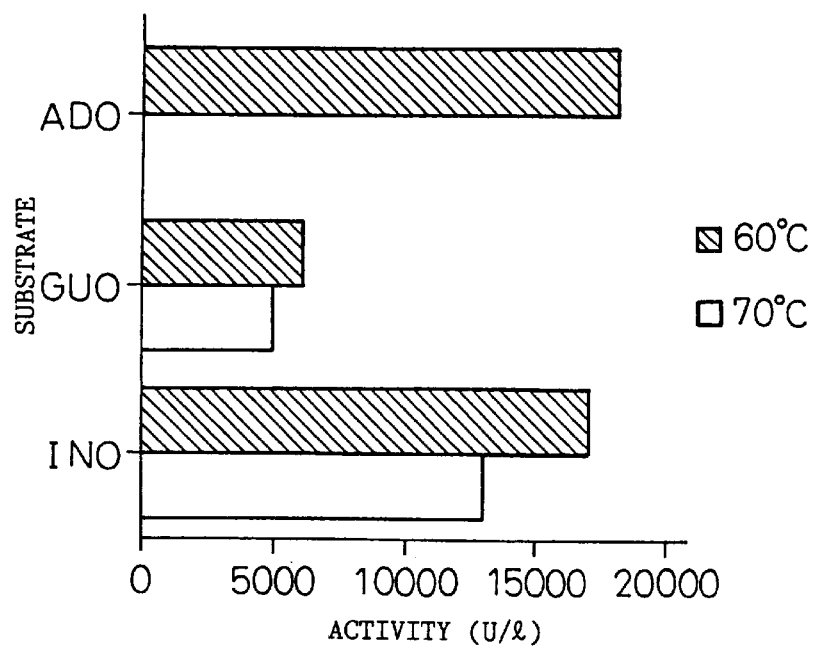
FIG. 7 shows the substrate specificity with respect to inosine, adenosine and guanosine at 60° C. and 70° C. and pH 5.0 by quantitative determination of reducing sugar.

Substrate specificity for inosine, adenosine and guanosine was investigated at 60° C. and 70° C. and at pH 5.0 by quantification of reducing sugars as shown in FIG. 7. As a result of activity to adenosine completely disappearing at 70° C., it was predicted from substrate specificity as well that there are at least two types of nucleosidases consisting of one that is able to decompose adenosine and one that is unable to decompose adenosine.

(5) Heat Inactivation

Figure 8:
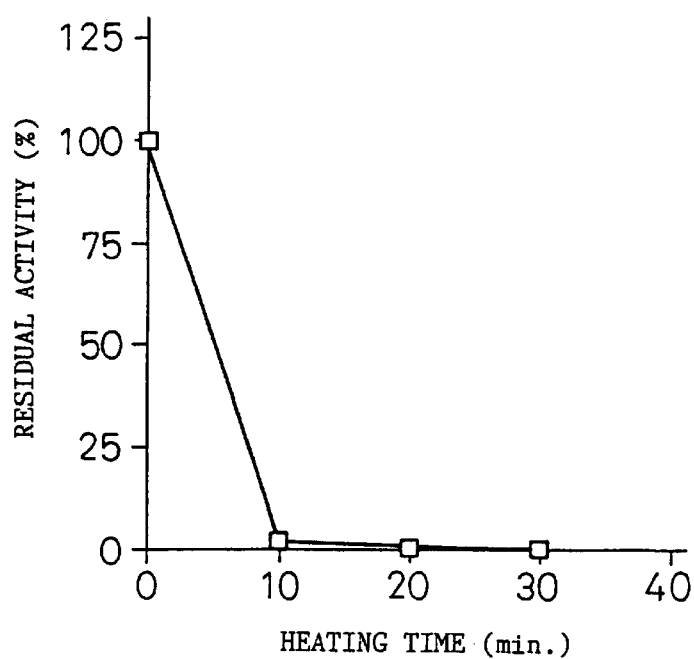
FIG. 8 shows the activity when inosine is used as substrate at 60° C. after incubating for each time at 100° C.

In order to investigate whether or not the present enzyme is inactivated by boiling the wort, after incubating at 100° C. for each time, the activity was investigated at 60° C. using inosine as substrate. Those results are shown in FIG. 8. Activity completely disappeared when incubated for 10 minutes at 100° C. Since the activity consisted of a nucleosidase that is able to decompose inosine and nucleosidase that is unable to decompose inosine at 60° C., both enzymes can be easily inactivated by boiling.

On the basis of the above results, it was found that the present enzyme has sufficient activity in the vicinity of pH 5.0, the pH of the wort, and has the ability to decompose adenosine at 60° C., and the ability to decompose inosine and guanosine at the high temperature of 80° C. In addition, since the enzyme is completely inactivated by boiling, active enzyme does not directly change the quality of the finished beer after the boiling step in the normal beer production process.

Example 4

Production of Nucleoside-Decomposed Barley Malt

Figure 9:
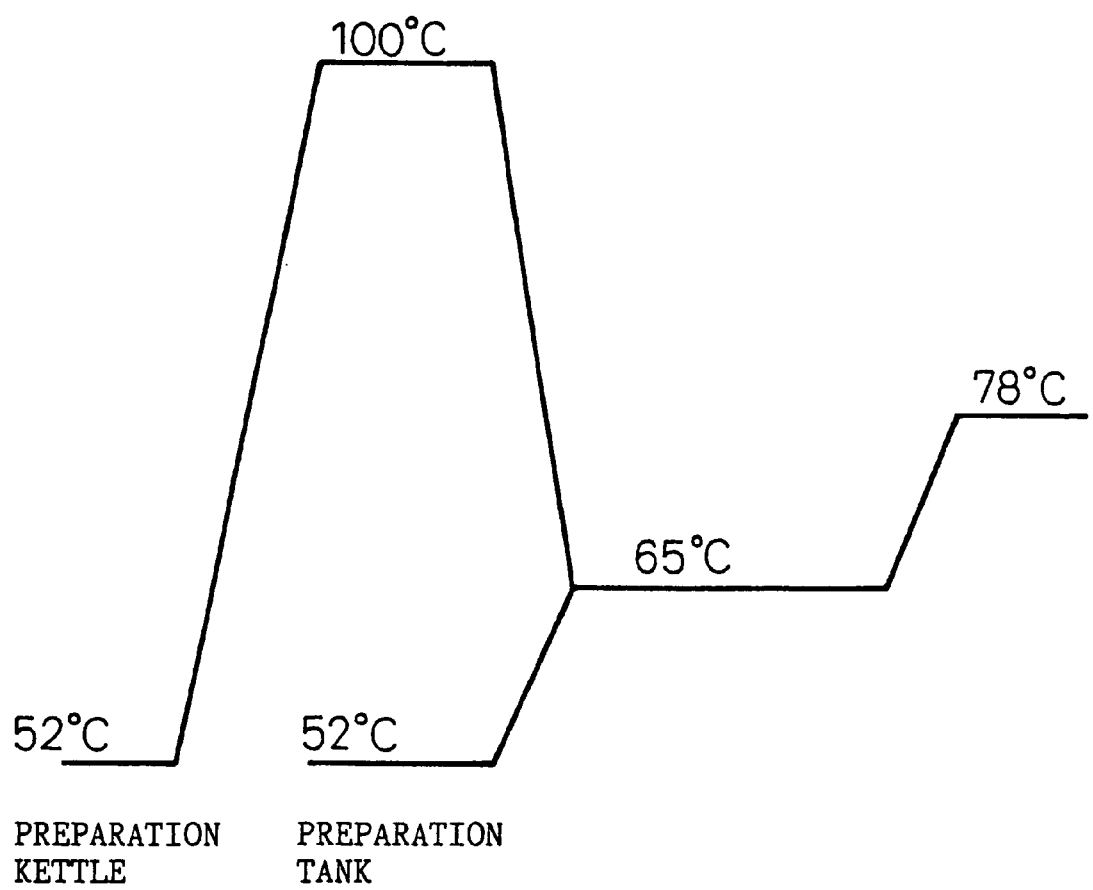
FIG. 9 shows the time-temperature curves of the preparation kettle and preparation tank in the wort production process.

The time-temperature curves of the preparation kettle and preparation tank in the wort production process are shown in FIG. 9. In addition, the blend ratios of the raw materials of the preparation kettle and preparation tank are shown in Table 3. In this production process, approximately 20,000 U of the nucleosidase of *Ochrobactrum anthropi* partially purified by heat treatment, salting out, ion exchange chromatography, gel filtration chromatography and so forth were added with the pulverized malt to produce the wort. The results of analyzing the purines contained in wort produced by adding enzyme and wort produced without adding enzyme are shown in FIG. 10. Purine nucleosides were not detected in the wort containing enzyme and the amount of purine bases increased. This wort is referred to as the nucleoside-decomposed wort.

TABLE 3

| Raw Materials | | Preparation Kettle | Preparation Tank |
|---|---|---|---|
| Malt | European | 6 kg | 12 kg |
| | American or Canadian | 6 kg | 12 kg |
| Water | | 42 liters | 84 liters |
| Calcium chloride | | None | 43 g |

Example 5

Beer Brewing using Nucleoside-Decomposed Wort

Figure 11A:
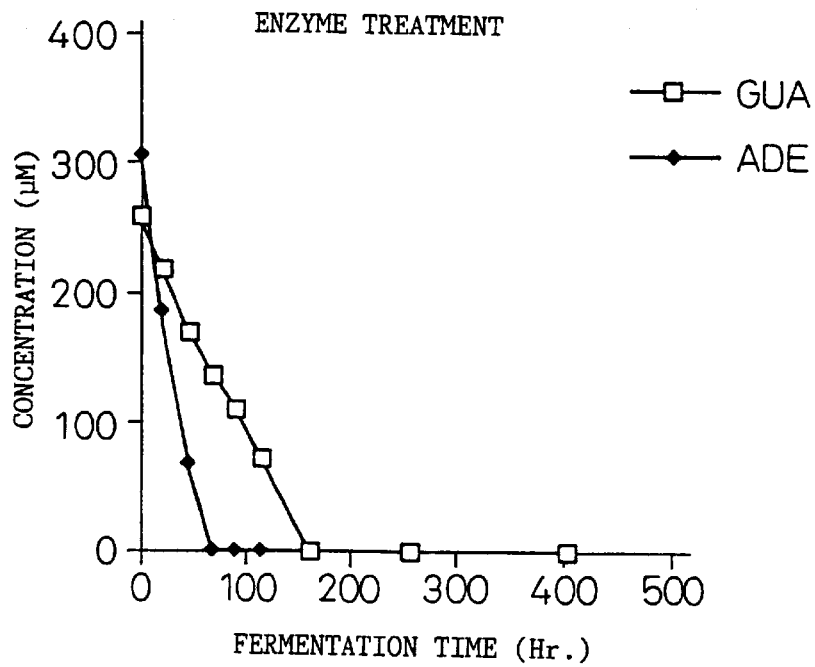
FIGS. 11A and 11B indicate the consumption of purines during fermentation using the nucleoside-decomposed wort produced in Example 4 and ordinary wort.
Figure 11B:
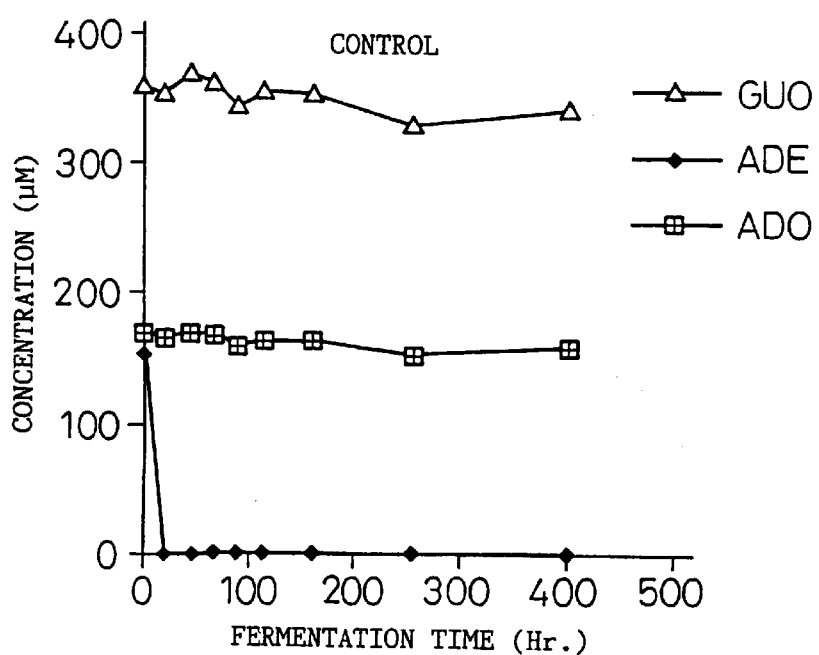

Beer was brewed using the nucleoside-decomposed wort produced in Embodiment 4 and normal wort. 10.5 g as wet weight of brewer's yeast were suspended in 2 liters of wort and fermented for 8 days at 12° C. The suspension was then stored for 5 days at 4° C. The consumption of purines during that fermentation is shown in FIG. 11. Adenosine was completely assimilated by the end of the fermentation period, and the amount of guanine in the ferment decreased with time, and was not detected at the completion of fermentation.

The balance of the guanine equivalent to roughly 90 $\mu$M was assimilated by the yeast. Thus, purines equivalent to a total of 260 $\mu$m in the wort were consumed in the fermentation process. The amount of purines of beer produced using wort produced without treating with enzyme was a total of 500 $\mu$M. Since the total amount of purines in beer brewed using wort treated with enzyme was 180 $\mu$M, it was possible to manufacture a beer in which the amount of purines was reduced by a total of 320 $\mu$M. Fermentation was virtually no different from that using ordinary wort both in terms of yeast growth and extract consumption, and there were also no large differences in terms of taste as well.

INDUSTRIAL APPLICABILITY

The present invention allows the obtaining of a beer in which the purine compound content in the beer is reduced by having purine bases metabolized by yeast in the fermentation process as a result of producing a beer from wort after obtaining a wort in which, among those purine compounds originating in the raw materials, purine nucleosides are decomposed into said purine bases so that said purine nucleosides are essentially not present, by allowing the enzyme of the present invention to act on said wort in the beer manufacturing process. Beer obtained by the process of the present invention is able to reduce the risk of morbidity of hyperuricemia, gout and so forth.

In the beer manufacturing process, the enzyme of the present invention is able to act on wort without changing that manufacturing process. In particular, when the enzyme of the present invention is allowed to act in the wort production process, since the temperature and pH in a normal wort production process (saccharification) are within the optimum ranges of the enzyme, the enzyme is able to act effectively, and said enzyme is able to act on said wort within the time required for the wort production process. In addition, since the enzyme can be deactivated in the boiling process of the wort which is immediately after the wort production process, the first step of the beer manufacturing process, the enzyme can be made to act more easily and economically. In addition, in the case of allowing the enzyme to act on the wort either immediately before fermentation or during fermentation, the enzyme can also be deactivated if the manufacturing process contains a heat treatment step after the fermentation process. Moreover, the resulting beer exhibits no large differences in terms of taste from ordinary finished beer, and it is possible to obtain a beer that is appealing as a finished beer product.

Information on the microorganism deposited in accordance with Regulation 13(2) of the regulations and Depository authority the Institute of Bioscience and Human-Technology Agency of Industrial Science and Technology:

Address: 1-1-3 Higashi, Tsukuba-shi, Ibaraki prefecture, Japan

Deposit number and deposition date: FERM BP-5377 Jan. 26, 1996

We claim:

1. In a process for manufacturing beer, the improvement comprising providing at least one member selected from the group consisting of an isolated purine nucleoside phosphorylase and an isolated purine nucleosidase to a wort, allowing said at least one member selected from the group consisting of an isolated purine nucleoside phosphorylase and an isolated purine nucleosidase to act on said wort, and employing said wort in a beer manufacturing process.

2. In a process for manufacturing beer, the improvement comprising providing at least one member selected from the group consisting of an isolated purine nucleoside phosphorylase and an isolated purine nucleosidase to a wort, allowing said at least one member selected from the group consisting of an isolated purine nucleoside phosphorylase and an isolated purine nucleosidase to act on said wort, wherein said at least one member selected from the group consisting of an isolated purine nucleoside phosphorylase and an isolated purine nucleosidase decomposes the purine nucleosides contained in the wort into purine bases, and employing said wort in a beer manufacturing process.

3. In a process for producing a wort, the improvement comprising providing at least one member selected from the group consisting of an isolated purine nucleoside phosphorylase and an isolated purine nucleosidase to a wort, and allowing said at least one member selected from the group consisting of an isolated purine nucleoside phosphorylase and an isolated purine nucleosidase to act on said wort.

4. In a process for producing a wort, the improvement comprising providing at least one member selected from the group consisting of an isolated purine nucleoside phosphorylase and purine nucleosidase to a wort, and allowing said at least one member selected from the group consisting of an isolated an isolated purine nucleoside phosphorylase and an isolated purine nucleosidase to act on said wort, wherein said purine nucleosides contained in the wort are decomposed into purine bases to obtain a nucleoside-decomposed wort.

5. A process according to claim 1 wherein said nucleosidase is a purine nucleosidase obtained from a microorganism having the ability to produce purine nucleosidase selected from the group consisting of the genera Ochrobactrum, Streptococcus, Pediococcus, Leuconostoc, Lactobacillus, Escherichia, Citrobacter, Serratia, Alcaligenes, Flavobacterium, Bacillus, Corynebacterium, Staphylococcus, Arthrobacter, Comamonas, Pseudomonas, Kluyveromyces, Saccharomyces, Debaryomyces, Pichia, Hansenula, Sporobolomyces, Sporidiobolus, Aspergillus and Pencillium.

6. A process according to claim 1 wherein the optimum pH range and optimum temperature range of said nucleoside phosphorylase or nucleosidase is 4.5–6.5 and 50° C.–80° C., respectively.

7. A process according to claim 1 wherein said nucleoside phosphorylase and/or nucleosidase is added to the wort before or during fermentation.

8. A process according to claim 1 wherein said at least one member selected from the group consisting of nucleoside phosphorylase and nucleosidase is allowed to act on said wort during the wort production process.

9. A process according to claim 4 wherein said nucleoside-decomposed wort does not contain purine nucleosides.

10. A process according to claim 3 wherein said nucleosidase is a purine nucleosidase obtained from a microorganism having the ability to produce purine nucleosidase selected from the group consisting of the genera Ochrobactrum, Streptococcus, Pediococcus, Leuconostoc, Lactobacillus, Escherichia, Citrobacter, Serratia, Alcaligenes, Flavobacterium, Bacillus, Corynebacterium, Staphylococcus, Arthrobacter, Comamonas, Pseudomonas, Kluyveromyces, Saccharomyces, Debaryomyces, Pichia, Hansenula, Sporobolomyces, Sporidiobolus, Aspergillus and Pencillium.

11. A process according to claim 3 wherein the optimum pH range and optimum temperature range of said nucleoside phosphorylase or nucleosidase is 4.5 to 6.5 and 50° C. to 80° C., respectively.

12. A process according to claim 3 wherein said at least one member selected from the group consisting of nucleoside phosphorylase and nucleosidase is allowed to act on said wort during the wort production process.

13. A process according to claim 2 wherein said nucleosidase is a purine nucleosidase obtained from a microorganism having the ability to produce purine nucleosidase selected from the group consisting of the genera Ochrobactrum, Streptococcus, Pediococcus, Leuconostoc, Lactobacillus, Escherichia, Citrobacter, Serratia, Alcaligenes, Flavobacterium, Bacillus, Corynebacterium, Staphylococcus, Arthrobacter, Comamonas, Pseudomonas, Kluyveromyces, Saccharomyces, Debaryomyces, Pichia, Hansenula, Sporobolomyces, Sporidiobolus, Aspergillus and Pencillium.

14. A process according to claim 2 wherein the optimum pH range and optimum temperature range of said nucleoside phosphorylase or nucleosidase is 4.5–6.5 and 50° C.–80° C., respectively.

15. A process according to claim 2 wherein said nucleoside phosphorylase and/or nucleosidase is added to the wort before or during fermentation.

16. A process according to claim 2 wherein said at least one member selected from the group consisting of nucleoside phosphorylase and nucleosidase is allowed to act on said wort during the wort production process.

17. A process according to claim 4 wherein said nucleosidase is a purine nucleosidase obtained from a microorganism having the ability to produce purine nucleosidase selected from the group consisting of the genera Ochrobactrum, Streptococcus, Pediococcus, Leuconostoc, Lactobacillus, Escherichia, Citrobacter, Serratia, Alcaligenes, Flavobacterium, Bacillus, Corynebacterium, Staphylococcus, Arthrobacter, Comamonas, Pseudomonas, Kluyveromyces, Saccharomyces, Debaryomyces, Pichia, Hansenula, Sporobolomyces, Sporidiobolus, Aspergillus and Pencillium.

18. A process according to claim 4 wherein the optimum pH range and optimum temperature range of said nucleoside phosphorylase or nucleosidase is 4.5 to 6.5 and 50° C. to 80° C., respectively.

19. A process according to claim 4 wherein said at least one member selected from the group consisting of nucleoside phosphorylase and nucleosidase is allowed to act on said wort during the wort production process.

* * * * *